United States Patent [19]

Barberet et al.

[11] Patent Number: Plant 6,571

[45] Date of Patent: Jan. 31, 1989

[54] CARNATION VARIETY 'LONDRAGEL'

[75] Inventors: Nicole Barberet; Yves Ducloux, both of Antibes, France

[73] Assignee: Laboratoire de Physiologie Vegetale de la Londe, La Londe, France

[21] Appl. No.: 889,845

[22] Filed: Jul. 28, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation cultivar particularly distinguished by its relatively small flowers of substantially white coloration, with a cast of very light yellow from the central portion of the bloom, borne singly on straight, strong stems of medium length and having rather abundant foliage, the flowers blooming recurrently and profusely during the growing season and the plant having a vigorous, upright growth habit reaching a height of about 104 cm. at eight months.

1 Drawing Sheet

BACKGROUND OF THE NEW PLANT

Our new carnation cultivar originated as a natural mutation of the carnation variety 'Loncruso' (U.S. Plant Pat. No. 5,514) and was discovered by us while inspecting the commercial production of the patent variety. We were immediately attracted by the very white coloration of the blooms characterized in an unusual manner by a cast of a very light yellow color coming from the inner portions of the flower petals. We felt that the small size of the substantially pure white flower would have good commercial merit and accordingly we propagated this sport by means of its cuttings with very satisfactory results in that the new plants appeared to be true reproductions of the original sport. Accordingly we directed that this new plant be propagated through several successive generations by means of cuttings of the next previous growth, which demonstrated that the distinctive characteristics of the original mutation would hold true from generation to generationand appeared to be firmly fixed.

DESCRIPTION OF THE DRAWING

Our new carnation cultivar is illustrated by the accompanying photographic drawing which shows, in full color, the upper portion of a typical spray stem bearing buds and blooms in various stages of development, the colors shown being as nearly true as it is reasonably possible to obtain by conventional photographic procedures.

DESCRIPTION OF THE NEW PLANT

The following is a detailed description of our new carnation variety based upon observation of greenhouse grown plants made at La Londe, Les Maures, France, early in 1986, the color designations being according to The R.H.S. Colour Chart published by The Royal Horticultural Soceity of London, England.

THE PLANT

Origin: Natural mutation.

Parentage: Carnation variety 'Loncruso' (U.S. Plant Pat. No. 5,514).

Classification:

*Botanic.*—*Dianthus caryophyllus.*

*Commercial.*—Spray carnation.

Form: A tall bush of erect spray shape and comprising at least four stems emitted near the ground from the main stem.

Height: Averages about 104 cm. at eight months.

Main stem:

*Length.*—Less than 15 cm. owing to pinching.

Branching character: Alternate.

Growth habit: Vigorous and upright with good strength.

Foliage:

*Quantity.*—Rather abundant.

*Number of leaves.*—More than 120.

*Size of leaf.*—Averages about 7.1 cm. long and about 1 cm. wide at the seventh node.

*Shape.*—Sessile and lanceolate with acute tip and curved margins.

*Texture.*—Leathery.

*Color.*—Upper side — 189A and 189B. Under side — 189A and 189B.

*Leaflets.*—None.

*Ribs veins and rachis.*—Hardly noticeable.

THE BUD

Size: Medium.

*Diameter.*—About 1.2 cm.

*Length.*—About 2.5 cm.

Shape: Long ovoid.

Color of petals: When sepals first divide and when petals begin to unfurl, the colors are the same as at full bloom.

Sepals:

*Number.*—Five.

*Shape.*—Joined at the lower part with somewhat acuminate tip. The sepals are hooded over the bud before dividing and stand up as the flower petals unfurl.

*Color.*—Inside — 145D. Outside — 138A/144C.

*Striae.*—Longitudinal.

Calyx:

*Size.*—Medium.

*Shape.*—Long cylindrical.

*Aspect.*—Smooth.

*Splitting.*—The calyx does not split.

Flower stem:

*Length.*—Averages about 53.6 cm.

*Character.*—Erect and rather thin.
*Color.*—189A/B.

THE FLOWER

Blooming habit: Recurrent and profuse during the blooming seasons with a tendency to give fewer blooms in fall.
Size of bloom: Small.
*Diameter.*—Averages about 5 cm.
*Depth.*—About 4.3 cm.
Borne: As a cluster with more than three flowers per stem.
Shape:
*When bloom first opens.*—High centered.
*When bloom matures.*—Dome shaped.
Petalage:
*Number of petals.*—Averages about 48.
*Arrangement.*—Imbricated.
*Form.*—Fan shaped and very finely serrated at outer end edges.
*Texture.*—Soft.
*Appearance.*—Satiny.
*Color.*—Both inner and outer petals: Body — Mainly 155B with inner portion cast of 3C. Base — Pale greenish yellow. Reverse side — Same as upper side.
Petaloids:
*Number.*—Less than six.
*Size.*—Smaller than petals.
*Color.*—The same as petals.
Flower stem:
*Length.*—Averages about 53.6 cm.
*Color.*—159A/B.
*Character.*—Upright and of good strength.
Persistence: The petals hang on and dry.

Fragrance: Hardly perceptible.
Disease resistance: Sensible to *Fusarium oxysporum* as observed I.N.R.A. Antibes, France.
Lasting quality:
*As a cut flower.*—At least ten days in vase keeping.

REPRODUCTIVE ORGANS

Stamens:
*Number.*—3 to 6.
*Arrangement.*—Around the ovary.
*Anthers.*—Size: Less than 4 mm. Color: Yellowish white.
*Filaments.*—Average length: About 2 cm. Color: Yellowish white.
Pistils:
*Number.*—Two.
*Styles.*—Length: In average, 2.3 cm. Color: Yellowish white.
*Stigmas.*—Color: Yellowish white.
Character of ovary: Rather globular.

This new spray carnation variety differs from 'Loncruso' (U.S. Plant Pat. No. 5,514), the parent plant, by its overall substantially white coloration with its light yellow case from the inner center portion of the flower and its lack of the red and red-purple marginal spotting very noticeable in the flowers of the parent variety.

We claim:

1. The new and distinct variety of spray carnation, substantially as herein shown and described, characterized by its profuse but recurrent flower production and its normal height of about one meter at eight months, the flower stem averaging about 53.6 cm. long when cut at the tenth node.

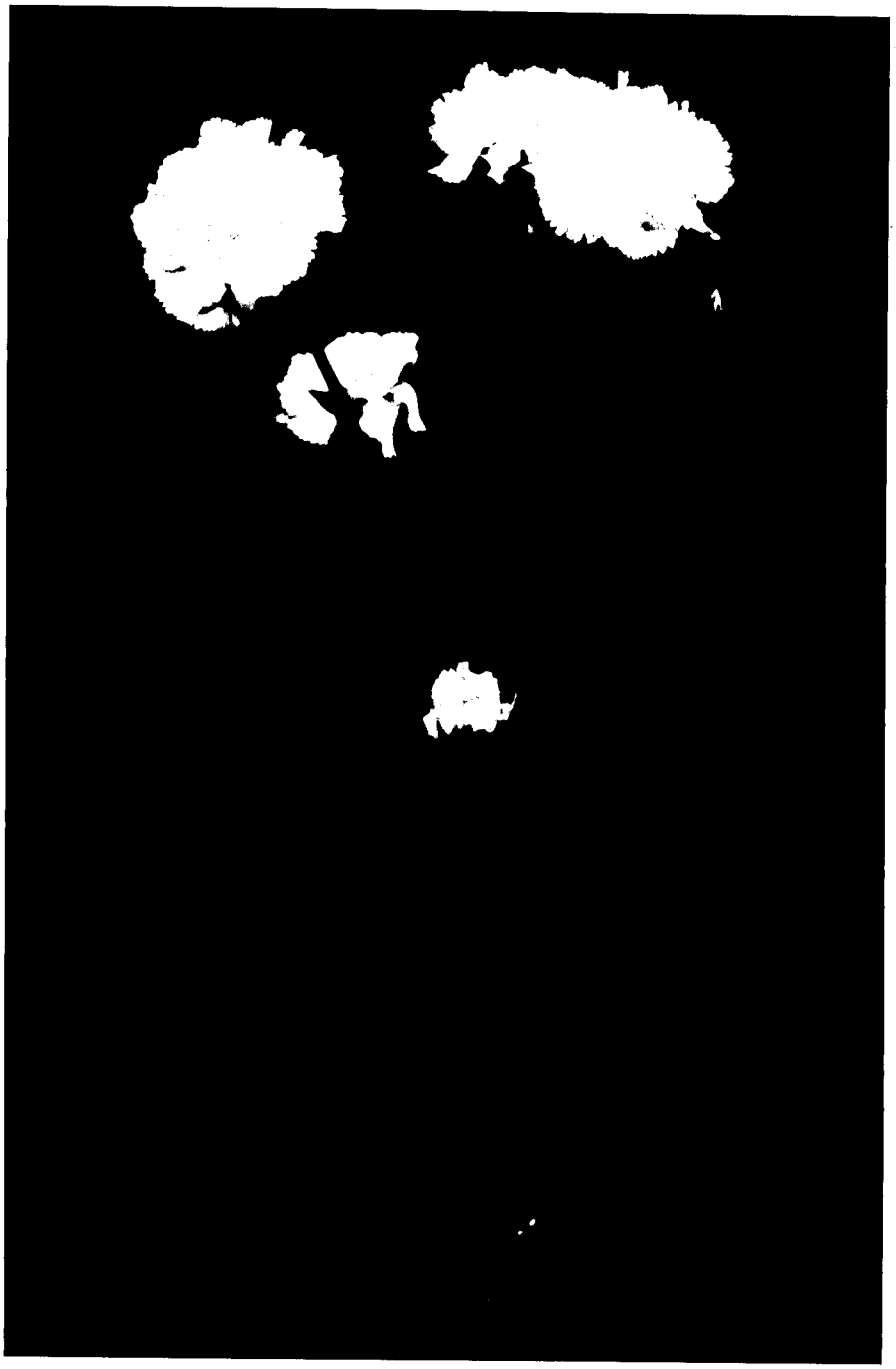

* * * * *